United States Patent
Campbell et al.

(10) Patent No.: US 7,041,506 B2
(45) Date of Patent: May 9, 2006

(54) PEPTIDES PROMOTING CELL ADHERENCE, GROWTH AND SECRETION

(75) Inventors: Robert L. Campbell, Bahama, NC (US); Mohammad Heidaran, Cary, NC (US); Catherine A. Spargo, Apex, NC (US); Jamie H. Wilkins, Durham, NC (US); Perry Haaland, Chapel Hill, NC (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 449 days.

(21) Appl. No.: 09/992,124

(22) Filed: Nov. 19, 2001

(65) Prior Publication Data

US 2003/0162289 A1    Aug. 28, 2003

(51) Int. Cl.
*A61K 38/08* (2006.01)
*A61K 38/18* (2006.01)
*C07K 7/06* (2006.01)
*C07K 17/00* (2006.01)
*C12N 5/06* (2006.01)

(52) U.S. Cl. .............. 435/402; 424/85.1; 435/404; 435/405; 514/12; 514/17; 514/21; 530/330; 530/345; 530/351; 530/397; 530/399; 530/409

(58) Field of Classification Search ............. 435/384, 435/402, 404, 405; 514/17, 21; 530/330, 530/345, 409
See application file for complete search history.

(56) References Cited

U.S. PATENT DOCUMENTS

| | | | | |
|---|---|---|---|---|
| 5,294,551 | A * | 3/1994 | Furcht et al. | 435/402 |
| 5,330,911 | A * | 7/1994 | Hubbell et al. | 435/402 |
| 5,411,956 | A * | 5/1995 | Miyazaki et al. | 514/15 |
| 5,563,215 | A * | 10/1996 | Bryhan et al. | 525/54.1 |
| 5,738,838 | A * | 4/1998 | Zamora | 424/9.341 |
| 5,834,029 | A * | 11/1998 | Bellamkonda et al. | 424/570 |
| 5,955,578 | A * | 9/1999 | Pierschbacher et al. | 530/345 |
| 6,100,380 | A * | 8/2000 | Green et al. | 530/328 |
| 6,121,027 | A * | 9/2000 | Clapper et al. | 435/180 |
| 6,552,249 | B1 * | 4/2003 | Cahoon et al. | 800/278 |
| 6,620,419 | B1 * | 9/2003 | Lintner | 424/401 |
| 6,759,510 | B1 * | 7/2004 | Haaland et al. | 530/330 |
| 2003/0045476 | A1 * | 3/2003 | Ruoslahti et al. | 514/16 |
| 2003/0104614 | A1 * | 6/2003 | Uhrich et al. | 435/325 |
| 2003/0175745 | A1 * | 9/2003 | Dean et al. | 435/6 |
| 2004/0072341 | A1 * | 4/2004 | Katinger et al. | 435/325 |
| 2005/0048588 | A1 * | 3/2005 | Calenoff et al. | 435/7.23 |

FOREIGN PATENT DOCUMENTS

| | | |
|---|---|---|
| WO | WO 87/00180 | 1/1987 |
| WO | WO 97/25999 | 7/1997 |
| WO | WO 99/46285 | 9/1999 |
| WO | WO 99/51254 A1 * | 10/1999 |
| WO | WO 00/02917 | 1/2000 |
| WO | WO 00/15188 A1 * | 3/2000 |
| WO | WO 02/02591 | 1/2002 |

OTHER PUBLICATIONS

Grahl-Nielsen et al. Oligopeptides As Sources Of Indispensible Amino Acids For Mammalian Cells In Culture. In Vitro. 1974, vol. 9, No. 6, pp. 414-420.*
Grahl-Nielsen et al. Synthesis of Oligomeric L-Lysine Peptides by the Solid-Phase Method. Biochemistry. Jan. 1969, vol. 8, No. 1, pp. 187-192.*
Katayama et al. A Pentapeptide from Type I Procollagen Promotes Extracellular Matrix Production. The Journal Of Biological Chemistry. May 15, 1993, vol. 268, No. 14, pp. 9941-9944.*
Payne. The Utilization of Prolyl Peptides by *Eschericia coli*. Biochemical Journal. 1971, vol. 123, pp. 255-260.*
Ramachandran et al. The Synthesis of L-Valyl-L-lysyl-L-valyl-L-tyrosyl-L-proline. The Journal Of Organic Chemistry. Jan. 1963, vol. 28, pp. 173-177.*
Rastogi et al. Augmentation of human natural killer cells by splenopentin analogs. FEBS Letters. Feb. 1993, vol. 317, No. 1,2, pp. 93-95.*
Yaron et al. Lysine Oligopeptides. Preparation by Ion-Exchange Chromatography. Biopolymers. 1972, vol. 11, pp. 607-621.*
Zahn et al. Glycyl-L-Lysyl-Glycyl-alpha-L-Glutamyl-Glycin. Annalen der Chemie. 1960, vol. 636, pp. 117-131.*
Tong, et al., Enhancing the neuronal interaction onfluoropolymer surfaces with mixed peptides or spacer group linkers, Biomaterials 22 (2001) 1029-1034.

* cited by examiner (Continued)

Primary Examiner—Jeffrey Edwin Russel
(74) Attorney, Agent, or Firm—Alston & Bird LLP

(57) ABSTRACT

The present invention provides specific peptides identified as having cell adhesion, growth, expression or secretion-enhancing activities. Many of the peptides of the invention may be produced in large quantity by such means as chemical synthesis or recombinant DNA methodology. They may be non-specifically adsorbed, or chemically attached to a surface or, alternatively, formulated in a culture medium to produce the desired effect on cultured cells.

90 Claims, 1 Drawing Sheet

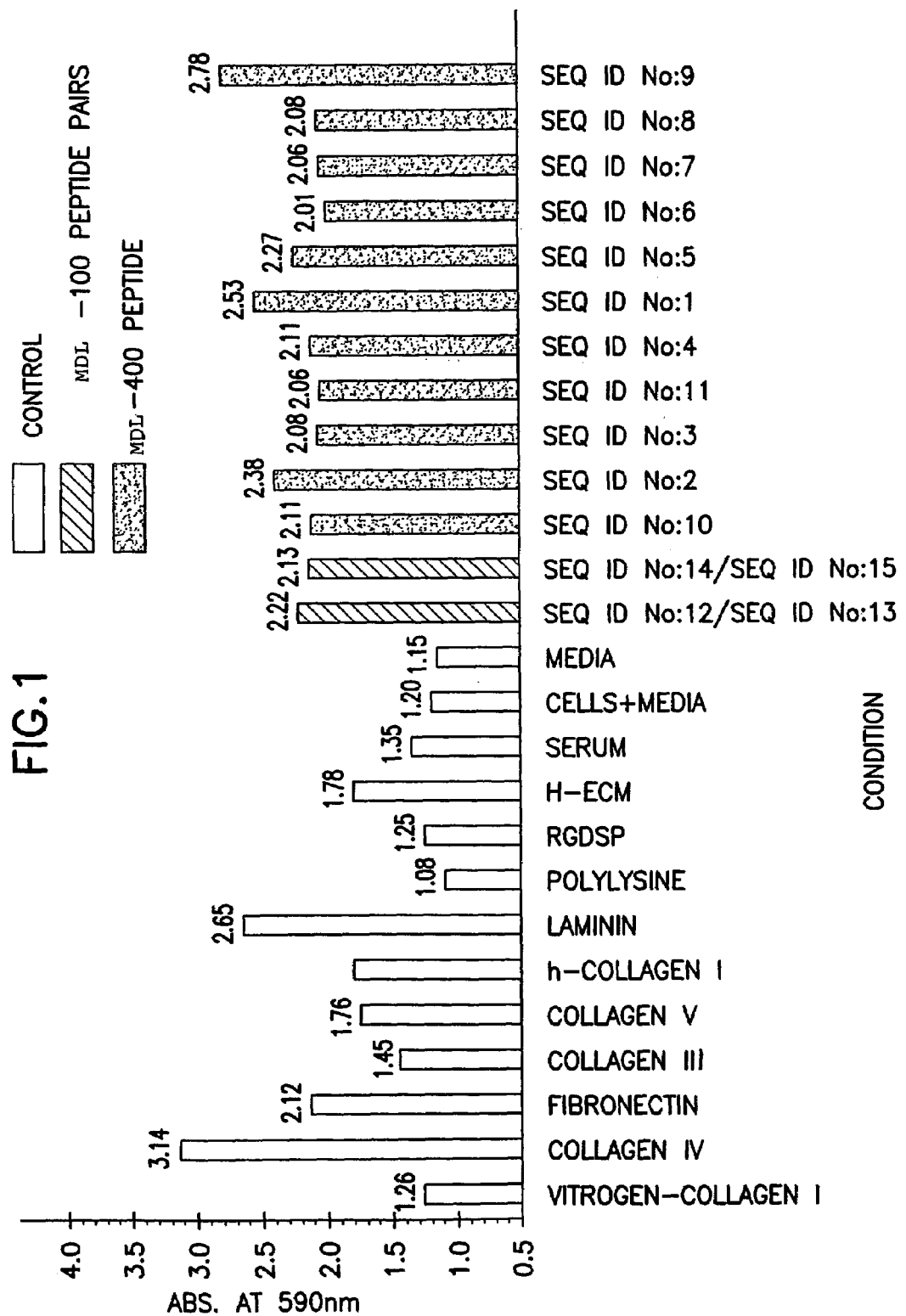

PEPTIDES PROMOTING CELL ADHERENCE, GROWTH AND SECRETION

BACKGROUND OF THE INVENTION

1. Field of the Invention

The present invention relates to peptides which affect the biological activity of cells in culture. In particular, the invention is directed to specific peptides affecting adherence, growth or secretion of cells.

2. Description of Relevant Art

Tissue and protein hydrolysates have been routinely used as a source of peptides in cell culture media since the late 1800's. They are the most common undefined culture media component in present use in bacteriology and often replace serum in the mammalian culture (S. Saha and A. Sen., *Aptavirol* 33:338–343, 1989). Hydrolysates and serum are not optimal sources of peptides for culture media. Further, their composition are undefined, vary from lot to lot and may harbor pathogens such as BSE.

It has been recognized that peptides are generally preferred nutrients for use in cell culture media as compared to their constituent amino acids. Several approaches have been taken in an effort to determine which specific peptides are utilized by a cell culture as a means for identifying defined peptides which affect growth or some other biological activity. For example, recent developments in peptide synthesis technology have made it possible to screen large numbers of compounds for media enhancement, either as individual defined sequences or as a mixture of variable sequences in a peptide library. The library approach has provided an opportunity to screen more peptide sequences for desired biological effects in cell culture. Once the sequence of a peptide having the desired biological activity is identified, it may be produced in large quantity, such as by chemical synthesis or recombinant DNA methods. Subsequently, the peptide can be included in a culture system by coating on a surface or being free in solution in the culture medium. Both presentations may lead to a desired effect on cultured cells.

The ability of cells to interact with components of the extracellular matrix in vivo is involved in several important biological processes including cellular growth, migration, and differentiation. Moreover, the necessity of anchorage-dependent cells to first adhere to surfaces largely dictates the success of a cell culture effort. In particular, the abilities of the cell to adhere, spread, and contract on solid matrices are prerequisites for the growth of normal anchorage-dependent cells in vitro. (Grinnell, F., Psychology, 53:67–149, 1978 and Couchman, et al., J. Cell Biol., 93:402–410, 1982) The ability of cells to adhere to surfaces is affected by many factors including the cell culture media used, the particular type of cell, and the particular surface upon which the cells are cultured. When the end goal is to accumulate product in the supernatant, and the cells being cultured are adherent-type cells, best results are typically achieved when adherence and growth are optimized first, followed by an optimization of expression and finally secretion.

In general, mammalian cells are cultured on polymer surfaces. Practically all mammalian cells that adhere to synthetic polymer surfaces are controlled by absorbed protein and are receptor mediated. For example, fibronectin is a protein component of the extracellular matrix which has been shown to be involved in the adhesion of mammalian cell types to tissue culture substrates. (Pearlstein, E., Nature, 262:497–500, 1976 and Kleinman, et al., Biochem. Biophys. Res. Commun., 72:426–432, 1976) The ability of fibronectin to aid in cell attachment has been localized to a trimer sequence (RGD), which is located in the cell binding domain of fibronectin.

Regarding the role of a cell culture substrate and other surfaces in promoting cell adhesion, it is known that proteins are immediately absorbed to the surface of a tissue culture substrate following placement of a protein solution thereon. Provided there are receptors for some of the absorbed proteins on the cell surface, and further provided that the conformation of the absorbed protein is not altered to a large degree by absorption so as to destroy ligand-receptor affinity, cell adhesions to the culture substrate and cell spreading can result.

With further reference to the role of the cell culture substrate and other surfaces in permitting cell adhesion, if cells are seeded on a substrate in the absence of absorbed protein, then proteins which are on the cell surface may directly absorb to the surface and the cell will, provided suitable conditions are present, secrete protein towards the surface in the form of an extracellular matrix. However, it is known that cells in culture never directly touch the surface except through intermediate absorbed protein.

It has been proposed that particular peptides are absorbed to a polymer surface in order to promote short-term cell adhesion to the surface. For example, Singer et al. proposed the absorption of a 13-mer peptide containing the RGD sequence described above onto a polymer substrate to promote cell adhesion. (Singer, et al., J. Cell Bio., 104:573–584, 1987) The disadvantages of using peptides of this length has been that they are highly subseptible to degradation at high temperatures such as those used during cell culture and to the proteolytic action of the cultured cells themselves.

An alternative to surface absorption of peptides to promote cell adhesions, has been to chemically attach peptides via covalent modifications to a surface. For example, Brandly, et al., (Analytical Biochemistry 173:270, 1988) proposed the inclusion of a 9-mer peptide in a polymer substrate to promote cell adhesions. While this method promoted cell adhesions, its required large concentrations of peptide to promote an acceptable level of cell adhesion. Given that the cost of preparing synthetic peptides is high, incorporation of peptides to the bulk of the polymer would not facilitate the economical preparation of cell culture substrates commercially.

It is also known to derivatize surfaces with peptides having less than 12 amino acid residues and containing one of the following sequences of amino acids: GRGD, GYIGSR, GREDV. These peptides have been further described as including a minimal cell-surface receptor recognition sequence, for example, RGD, YIGSR, or REDV to permit the cell receptor mediated support of cells to a treated surface. The peptides are preferably attached to the surface through the reaction of a terminal primary amine associated with the peptide to be grafted to the surface and an active group on the polymer surface. A disadvantage of this method is that the surface must first be activated before the surface can be derivatized with a peptide. The process used for activating the surface can be lengthy in time and can involve reagents which may be toxic to cells, requiring thorough washing of the surface prior to modification with the peptide and prior to culturing of the cells on the derivatized surface. Further, the efficiency of peptide immobilization is highly dependent on the prior polymer derivatization process. The final range of peptide concentration and orientation on the surface are restricted.

Thus, a need exists in the art for the discovery of additional small peptides for use in modifying surfaces to promote cell adhesions and growth which are thermally stable and resistant to proteolysis by cellular proteases or proteases such as trypsin which are often added to remove adherent-type mammalian cells from a tissue culture substrate. It is further desired that the small peptides are resistant to the desorptive effect, but not require covalent immobilization to the surface.

There is also a need in the art for small peptides that enhance expression and secretion. Adherent cell lines are often the choice for production when the target pharmaceutical is secreted. Having an immobilized cell allows one to easily remove the high molecular weight constituents, which are present in the supernatant and required during the growth phase, and to subsequently replace the supernatant with a stabilizing media containing only low molecular weight substances that will not co-purify with the target pharmaceutical. Unfortunately, these stabilizing media often reduce expression and secretion levels. Having low molecular weight peptides that increase accumulation of product in tissue culture broth would therefore be advantageous.

Finally, there is a need for peptide libraries which accelerate the discovery of media or culture environment constituents with the attributes described above. The ability to match peptide performance with physical properties will lead to peptide classes delivering benefits across many cell types and culture conditions. Further, such peptide classes will allow bioengineers to rapidly identify high-performing bioactive peptides as media constituents for cells in rare supply, such as stem cells.

SUMMARY OF THE INVENTION

The present invention provides peptides identified as having cell growth and/or and secretion enhancing properties. Specific peptides having these enhancing properties may be produced in large quantity by such means as chemical synthesis or expression by recombinant DNA methods and may be, for example, adsorbed to a surface in a cell culture system or, alternatively, formulated in a culture medium to produce the desired effect on cultured cells.

In particular, the invention provides peptides which enhance cell growth and/or secretion in a cell culture system which include a structure of at least one of (a) xxxkx, (b) xxkxx, (c) xxxxk, (d) xkxxx and (e) kxxxx, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof.

Further provided by the invention is a peptide which enhances cell growth and/or secretion, the peptide including a structure of at least one of (a) xxxkx, (b) xxkxx, (c) xxxxk, (d) xkxxx, and (e) kxxxx, wherein each x may be the same or different hydrophobic or uncharged polar amino acid residue and k represents lysine.

Specific inventive peptides with adhesion and/or growth-promoting activities include peptides having an amino acid sequence selected from the following: IFFKG (SEQ ID NO:1), FIKFG(SEQ ID NO:2), FIFAK(SEQ ID NO:3), QVVAK(SEQ ID NO:4), FKFIG(SEQ ID NO:5), AFFKI (SEQ ID NO:6), VFPFK(SEQ ID NO:7), AKIFF(SEQ ID NO:8), AFKIF(SEQ ID NO:9), KFAFI (SEQ ID NO:10) and FAKFI(SEQ ID NO:11) and combinations thereof.

In a further aspect of the present invention, a peptide composition is disclosed which promotes adherence and/or growth of adherent-type cells on a surface including one or more pairs of peptides selected from the following group: (a) AFFFQ(SEQ ID NO:12)/EEEMY(SEQ ID NO:13) and (b) FIKLM (SEQ ID NO:14)/FFIPY (SEQ ID NO:15).

Specific inventive peptides with secretion-enhancing activities include peptides having an amino acid sequence selected from the following: FKLVY(SEQ ID NO:16), KKKKK(SEQ ID NO:17), KKKKL(SEQ ID NO:18), FKKKQ(SEQ ID NO:19), FKFIG(SEQ ID NO:5), KKKSK (SEQ ID NO:20), KKKLK(SEQ ID NO:21), FKKKK(SEQ ID NO:22), LKKKK(SEQ ID NO:23), KKLKK (SEQ ID NO:24), KKKKT(SEQ ID NO:25), KKPKK(SEQ ID NO:26), KKPQY(SEQ ID NO:27), SKKKK(SEQ ID NO:28), KVKKK(SEQ ID NO:29), KNQTY(SEQ ID NO:30), FKKKV(SEQ ID NO:31), KPKKK(SEQ ID NO:32), FFKKK(SEQ ID NO:33), HKNQT(SEQ ID NO:34), FKLVG(SEQ ID NO:35), KKQPK(SEQ ID NO:36), EKKQT(SEQ ID NO:37), EKKKK(SEQ ID NO:38), KKIKQ(SEQ ID NO:39), KKKKS(SEQ ID NO:40), KKQKK(SEQ ID NO:41), KKLNY(SEQ ID NO:42), DGKKT(SEQ ID NO:43), KKPTT(SEQ ID NO:44), KFIFG(SEQ ID NO:45), FKKMY(SEQ ID NO:46), FFFKK(SEQ ID NO:47), KQKKI(SEQ ID NO:48), HIKKK(SEQ ID NO:49), DFFHK(SEQ ID NO:50), AKKKK(SEQ ID NO:51), AHIKK(SEQ ID NO:52), AHKKK(SEQ ID NO:53), LKLVY(SEQ ID NO:54), PKQKK(SEQ ID NO:55), AKKKT(SEQ ID NO:56), DEETY(SEQ ID NO:57), HNPPY(SEQ ID NO:58), GGHMS(SEQ ID NO:59), AADEG(SEQ ID NO:60), GGGGS(SEQ ID NO:61), EEGLS(SEQ ID NO:62), HHPST(SEQ ID NO:63), FHHNT(SEQ ID NO:64), ADELN(SEQ ID NO:65), KKKK(SEQ ID NO:66), KKK (SEQ ID NO:67), KK(SEQ ID NO:68), OrnOrnOrn(SEQ ID NO:69), RRR(SEQ ID NO:70) and combinations thereof.

Cell culture substrates are provided by the invention, the substrate including one or more of the inventive peptides represented by SEQ ID NO:1 through SEQ ID NO:11 and SEQ ID NO:16 through SEQ ID NO:70 described above. Moreover, inventive cell culture substrates may include one or more of the pairs of peptides identified above as (a) (SEQ ID NO:12)/(SEQ ID NO:13) and (b) (SEQ ID NO:14)/(SEQ ID NO:15).

Further provided by the invention is a cell or tissue culture medium including the peptides or peptide compositions of the present invention described above.

The invention provides peptide libraries which are useful for rapid identification of biologically active peptides wherein the peptide library is selected from the following group of libraries: (a) xxxkx, (b) xxkxx, (c) xxxxk, (d) xkxxx, (e) kxxxx and permutations thereof, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof. Once active peptides for a particular cell type are identified in an inventive peptide library, a smaller library of peptides possessing the core features (charge, size hydrophobicity) can then be generated and applied to new cell systems, thereby reducing the number of compounds that must be screened.

The invention further provides a peptide which enhances cell secretion in a cell culture system, wherein all amino acids of the peptide possess positively charged side chains.

Also provided is a method of modifying a surface in a cell culture system so as to enhance cell growth and/or secretion in the system, including the step of applying to the surface a peptide including a structure selected from the following group: (a) xxxkx, (b) xxkxx, (c) xxxxk, (d) xkxxx, (e) kxxxx and combinations thereof, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof.

In a further aspect of the invention, a method of adhering cells to a surface to promote cellular growth is disclosed including the steps of (i) providing a surface at least partially coated with a peptide including a structure selected from the following: (a) xxxkx, (b) xxkxx, (c) xxxxk, (d) xkxxx, (e) kxxxx and combinations thereof, wherein each x may be the same or different hydrophobic or uncharged polar amino acid residue and k represents lysine; and (ii) contacting the at least partially coated surface with the cells for a sufficient time to permit cellular attachment thereto.

Lastly, the invention provides a method for enhancing cellular growth and/or secretion, which includes the step of culturing cells or tissues in the presence of the peptides or peptide compositions of the present invention.

BRIEF DESCRIPTION OF DRAWING

FIG. 1 is a graphical representation of the results of an oxygen biosensor assay which was used to monitor growth of MC3T3 cells. Inventive peptides were identified in an intitial maximum diversity library (MDL-100) and a follow-up MDL-400 library comprised of compounds filling in the property space coarsely covered by the MDL-100. Biological effects on the cells is compared in the presence and absence of the inventive peptides and in presence and absence of extracellular matrix (ECM) controls and known peptide controls. The absorbance at 590 nm is a measure of relative oxygen consumption, which correlates with cell growth.

DETAILED DESCRIPTION OF INVENTION

By the term "enhancing secretion", "promoting secretion", and the like, it is meant that the level of a target molecule in the supernatant medium is greater in the presence of one or more of the inventive peptides relative to in its absence. This effect may be related to a number of factors including, but not limited to, changes in protein expression levels and intracellular trafficking.

Two initial peptide maximum diversity libraries, MDL-400 and MDL-100 and a follow-up library comprised of compounds related to early leads were constructed using conventional peptide synthesis techniques. The candidate peptides in the follow-up library were selected by "Nearest Neighbor" techniques. They were subsequently screened for biologically active peptides exhibiting certain desired characteristics. One goal of the present work was to identify peptides which when non-covalently attached or non-specifically adsorbed to a surface could increase cell growth as measured by an increase in oxygen consumption of the cultured cells, where the increase in oxygen consumption was measured by use of an oxygen biosensor. A second goal was to identify peptides enhancing secretion. In particular, a cell line secreting platelet derived growth factor was selected and supernatant levels of PDGF were monitored by a sandwich ELISA. The MDL libraries were first screened for their effect on PDGF secretion and then additional leads were found in a follow-up library comprised of Nearest Neighbors. Further analysis uncovered bioactive isomer sets which were determined to enhance growth.

Each library of initial peptide candidates was selected based on specific design criteria, including charge, molecular weight, mass and hydrophobicity. Table A below classifies amino acids on the basis of the polarity of their side chains.

TABLE A

| Hydrophobic | Uncharged Polar | Positively Charged | Negatively Charged |
|---|---|---|---|
| alanine | serine | lysine | aspartic acid |
| leucine | threonine | arginine | glutamic acid |
| isoleucine | tyrosine | histidine | |
| valine | asparagine | | |
| proline | glutamine | | |
| phenylalanine | cysteine | | |
| tryptophan | glycine | | |
| methionine | | | |

Each peptide from the MDL and Nearest Neighbor follow-up libraries consisted of five amino acid residues. Selection of amino acids to form library peptides was typically based on ease of synthesis.

The clear majority of PDGF secretion enhancing sequences (SEQ ID NO:16 through SEQ ID NO:56 and SEQ ID NO:5) had one of the following structures: (a) xxxkx, (b) xxkxx, (c) xxxxk, (d) xkxxx, (e) kxxxx, wherein k represents lysine and each x may be the same or different amino acid selected from the following residues: lysine, alanine, isoleucine, phenylalanine, proline, valine, glycine, glutamine, leucine, methionine, asparagine, serine, threonine, tyrosine, aspartic acid, glutamic acid, histidine and derivatives thereof. Screening a smaller number of MDL peptides for growth led to the same common structures: (a) xxxkx, (b) xxkxx, (c) xxxxk, (d) xkxxx, (e) kxxxx wherein each x may be the same or different amino acid independently selected from the following hydrophobic or uncharged polar residues: phenylalanine, isoleucine, alanine, valine, proline, glycine and glutamine and k represents lysine. For both growth and secretion screening, a smaller number of unrelated bioactive compounds without lysine were found.

To identify peptides in a particular library which positively affected cell expression and secretion, each test peptide was added to a well containing a monolayer of chinese hamster ovary cells. The selected cells were anchorage-dependent CHO cells known to secrete platelet derived growth factor, which were initially grown on the tissue culture surfaces using a media with serum. After the monolayer was established, a chemically defined base media and a single test peptide was added to each well. In the present work, secretion of PDGF was assessed in the presence and absence of peptides from the library by collecting supernatant from each well and performing an ELISA specific for PDGF on the supernatant. The output was the absorbance at 492 nm. Secretion was evaluated in a basal medium rich in amino acids, the necessary vitamins, metals, carbon source and concensus CHO culture factors. PDGF levels were compared to known standards spiked into the media used for culture.

Specific inventive peptides with secretion enhancing activities include peptides having an amino acid sequence selected from the following: SEQ ID NO:16, SEQ ID NO:17, SEQ ID NO:18, SEQ ID NO:19, SEQ ID NO:5, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70 and combinations thereof.

To identify peptides in a particular library which positively affected cell growth in cell culture, the library was screened in a growth assay. The selected cells were anchorage-dependent MC3T3 cells, which were grown on tissue culture surfaces which had been pre-coated with peptides of the present invention. The screening medium used to evaluate peptides in the library was a low serum medium allowing evaluation of peptide effects with low interference from undefined materials present in the medium. In the present work, growth of MC3T3 cells was assessed in the presence and absence of the peptides in the library which were present in the form of a dried film on a tissue culture substrate. Growth was evaluated in a basal medium rich in amino acids and containing the necessary vitamins, metals and simple carbon source. After an appropriate incubation time, growth of each peptide-supplemented culture is compared to growth of the unsupplemented culture. The extent of growth was evaluated using a Becton Dickinson oxygen sensor to detect oxygen consumption by the cells. The cell number in each well containing a particular peptide was then assessed indirectly with a flurometer which measured fluorescence generated from a fluoroescent dye using band-pass filters of 465 nm for excitation and 590 nm for emission.

Briefly, the oxygen biosensor is based upon the fluorescence of ruthenium dye which is quenched in the presence of oxygen. The dye is immobilized within an inert but highly permeable silicone matrix located at the bottom of microtiter wells. Previous data suggested that increased oxygen consumption correlates with an increase in cell number. (Wodnicka, M., Guarino, R. D., Hemperly, J. J. Temmins, M. R., Stitt, D. and Pitner, J. B. (2000) J. of Biomolecular Screening 5:141–152)

Several peptides which enhanced cell growth were identified in the initial screening of the MDL-400 peptide library. These peptides included the following: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11 and combinations thereof. In particular, as described in further detail below, each of these peptides, when adsorbed to a surface, produced a significant difference in growth as compared to cells grown on an uncoated surface.

Two inventive peptide compositions were further identified to have growth enhancing properties. These compositions were selected during screening of a library designated MDL-100. The specific pairs of peptides identified were the following: (a) SEQ ID NO:12/SEQ ID NO:13 and (b) SEQ ID NO:14/SEQ ID NO:15.

Canonical peptides or isomers have the same amino acid composition and only the sequence varies. When multiple canonical peptides are found to create an enhancement, a broad non-specific mechanism is implied. Herein, a library of peptides were initially screened for improvements to PDGF expression in CHO cells. The canonicals FKFIG (SEQ ID NO: 5) and KFIFG (SEQ ID NO: 45) were found to be positive for PDGF. Members of the same canonical set were later screened for the impact on MC3T3 growth. Based on this growth screening, FKFIG (SEQ ID NO: 5) and two other members of the canonical set, IFFKG (SEQ ID NO: 1) and FIKFG (SEQ ID NO: 2) were found to be positive. The results are shown in Tables 1, 3, and FIG. 1. The results identify a new class of compounds useful for cell culture.

As described above, the present invention provides a peptide which enhances cell growth and/or secretion in a cell culture system, wherein the peptide includes a structure of at least one of (a) xxxkx, (b) xxkxx, (c) xxxxk, (d) xkxxx, and (e) kxxxx, wherein k is represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof.

It is well within the contemplation of the present invention that peptides of the invention which promote cell growth and/or secretion in a cell culture system may contain greater than five amino acid residues, provided that they include within their sequence a structure corresponding to at least one of (a) xxxkx, (b) xxkxx, (c) xxxxk, (d) xkxxx, and (e) kxxxx described above, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof. It is noted, however, that care must be given to the action of endogenous and exogenous proteases within the culture system. Such proteases are more likely to degrade peptides of longer length which may include protease cleavage sites within their sequence. Moreover, whole proteins or large peptides are more susceptible to degradation.

It is noted that pentapeptides according to the present invention would be generally free of internal protease cleavage sites. However, with respect to the desirable methods for producing the peptides of the invention, it would be particularly desirable to select peptides that include C-termini or N-termini corresponding to the C-termini and N-termini produced by enzymatic or chemical cleavage of proteins in traditional culture media hydrolysates. For example, the inventive peptide QVVAK(SEQ ID NO:4) does not have an internal trypsin site but does possess a C-terminal lysine which can be leveraged to manufacture the peptide economically as a concatemer in numerous recombinant production systems known in the art. As contactemers may contain hundreds of copies of the coding sequence. Concatemer nucleic acid constructs encoding peptides of the invention with C-termini and N-termini which are subject to enzymatic or chemical cleavage, produce polypeptides comprising repeating subunits of the peptide amino acid sequence separated by convenient cleavage sites. Cleavage using the appropriate enzymatic or chemical means releases the peptide monomer. This approach to manufacture increases the yield of the desired peptide and decreases manufacturing costs. Post-expression processing is simplified due to the cleavage site made available by cloning of the concatemer structure.

The invention also encompasses a peptide which enhances cell growth and/or secretion, the peptide comprising a structure of at least one of (a) xxxkx, (b) xxkxx, (c) xxxxk, (d) xkxxx, and (e) kxxxx, wherein each x may be the same or different hydrophobic or uncharged polar amino acid residue and k represents lysine. In one embodiment, the hydrophobic or uncharged polar residue is selected from the group consisting of Phe, Ile, Ala, Val, Pro, Gly, Gln, Tyr, Thr, Leu and derivatives thereof.

Peptides of the present invention may be synthesized by any suitable method known in the art, such as FMOC Chemistry of Atherton and Sheppard, 1989 in Solid Phase Peptide Synthesis (Merrifield 1965). Boc chemistry may also be used as well as synthesis on a variety of different solid supports, "tea-bag" synthesis (Houghten), and split and divide combinatorial methods. Solution phase methods for peptide synthesis may also be used.

As an alternative to chemical synthesis, the peptides of the present invention can be produced more economically using recombinant methods. For recombinant production, the peptide sequence is first converted to a corresponding nucleic acid sequence which encodes the amino acid sequence of the peptide. This may be an RNA sequence which is subsequently translated to produce the peptide, or it may be a DNA sequence which is then cloned into an expression vector under the control of a promoter which enables the transcription of the DNA sequence and subsequence translation of the mRNA to produce the peptide. Many such methods for recombinant production of the desired peptide or protein sequence are well known to the practitioner and may be applied to the production of the peptides of the invention without the exercise of inventive skill. The peptides may be purified, if necessary, also using standard methods for physical, chemical and affinity separation which are well known to the practitioner.

Useful peptides of the invention may include modifications to the C-terminus, (e.g., amides and esters), the N-terminus (e,g., acetyl groups) and non-naturally occurring amino acids as will be described in further detail below, (e.g. norleucine). Such modifications may have an effect on peptide activity. Moreover, modifications may provide a means for covalent attachment to a carrier or linker molecule.

The peptides of the invention may be included in tissue culture media prepared for prokaryotes and yeast, as well as cultured cells and tissues derived from vertebrates and invertebrates to produce a desired effect on the cells, such as increased adherence, growth and/or expression and secretion. The base culture medium to which the peptide is added may be a chemically defined medium or a complex medium containing undefined components such as fetal calf serum or yeast hydrolysates. However, chemically defined or semi-defined media are preferred, as the peptide of the invention are most advantageously used as a means for reducing or eliminating performance variability due to undefined media components and for reducing or eliminating animal-derived components in the media used to produce pharmaceutical products.

It is within the ordinary skill in the art to determine an appropriate concentration of an inventive peptide in a selected culture medium or coating solution. In one embodiment, the peptide is introduced into a cell culture system at a concentration of about 500 µM to about 6 mM. In a further embodiment, the peptide is introduced into a cell culture system at a concentration of about 250 µM to about 24 mM. In yet another embodiment, the peptide is introduced into a cell culture system at a concentration ranging from 3 mM to about 12 mM. Moreover, multiple peptides may be added to a culture medium or to a solution for coating a surface to produce a synergistic effect (if those have the same effect on the cells) or to produce multiple effects (if each peptide has a different effect on the same cells).

Those skilled in the art will appreciate that the ability of the peptides of the present invention to enhance cellular adherence, growth, expression or secretion may be affected by the base culture medium and/or the presence of other medium components. The culture medium can be used to culture any cell, tissue, or organ of interest. Preferably, the culture medium is a cell culture medium. Typically, and preferably, peptides of the present invention may be used as components of culture medium to culture cells in vitro. In particular, the present invention can be practiced to culture animal, (more preferably mammalian, avian or insects), plant, bacterial, protozoan, fungal, or yeast cultures. In addition, the culture medium can be one that is used to package viruses or bacteriophage in host cells. A culture medium according to the present invention may also be useful for culturing a primary cell (e.g., to grow beta-islet cells for insulin production). Other uses for a medium containing the peptide of the present invention, include use in the culture of cells that have been genetically engineered to express recombinant peptides or protein. Finally, the culture medium can be a liquid, semi-solid or solid culture medium. Preferably, the culture medium is a liquid medium.

The peptides of the invention may be dissolved in a carrier such as water to produce a solution for coating tissue culture substrate or other surfaces for growth of anchorage-type cells. For example, a solution containing one or more peptides of the invention may be distributed onto a surface and dried in a reverse airflow hood that results in a peptide being present on the surface in the form of a dried film.

In one embodiment of the present invention, the peptide increases oxygen consumption of cells. For example, peptides of the invention, when adsorbed to a surface in the form of a dried film, were found to enhance cell growth when compared to growth obtained on uncoated surfaces as measured by an increase oxygen consumption of the cells. Peptides of the invention may enhance growth of cells in vitro or in vivo. For example, tissue culture surfaces may be treated to enhance the growth of the cells in vitro or, alternatively, peptides may enhance the growth of cells in vivo on the surface of an implanted biomedical device.

In a further embodiment, cells are selected from the group including, but not limited to, the following: epithelial, endothelial, dermal, neural, tumor, lymphocytic, stem cells, and combinations thereof. In general, peptides of the invention are useful in promoting adherence and growth of anchorage-dependent cells.

The mode of attachment of the peptides of the invention to a surface includes non-covalent interaction, non-specific adsorption, and covalent linkages. In one embodiment of the invention, the peptide may be adsorbed directly to a surface. In a further embodiment, the peptide may be adsorbed to a surface which has already been precoated with, but is not limited to, at least one of the following: bovine serum albumin, ovalbumin, keyhole limpet haemocyanin, collagen, fibronectin, laminin, polylysine, a peptide having a cell-surface receptor recognition sequence, an immunoglobulin, a polysaccharide, or a growth factor. In another embodiment, the peptide and one of the proteins described above are applied simultaneously, either free or as a conjugate to the surface.

The growth enhancing peptides of the present invention are suitable for promoting adherence and growth of a variety of anchorage-dependent cells on surfaces, including two dimensional or three dimensional surfaces. For example, the surface may be that of a bioreactor which allows cells to attach in 3-D arrays. More efficient bioreactors than presently exist can be designed by attaching the cells to 3-D surfaces modified with the inventive peptides.

With specific reference to the types of surfaces which may be used in the practice of the present invention, suitable surfaces would include, but are not limited to, ceramic, metal or polymer surfaces. Most desirably, the present invention is used in the treatment of polymer surfaces and ceramic, e.g. glass surfaces. Suitable surfaces for use in the present invention, include, but are not limited to, plastic dishes, plastic flasks, plastic microtitre plates, plastic tubes, sutures, membranes, films, bioreactors, and microparticles. Polymer surfaces may include, but are not limited to, poly(hydroxyethylmethacrylate), poly(ethylene terephthalate), poly(tetrafluoroethylene), fluorinated ethylene, poly (dimethyl siloxane) and other silicone rubbers. Glass surfaces may include glycerol propylsilane bonded glass.

According to one specific embodiment of the invention, the peptide can be bound to a carrier. A precondition for selection of a suitable carrier molecule is that the functional biological activity of the peptides should not be impaired either by the carrier or by the coupling process. Carrier molecules for the purposes of the invention can belong to varied classes of substances, including, but not limited to, protein components of the extracellular matrix such as fibronectin, collagen, and laminin. Moreover, the peptide may be covalently linked to more defined substances including, but not limited to, polylysine, ovalbumin, bovine serum albumin, keyhole limpet haemocyanin, immunoglobulin, polysaccharide, lipoprotein, growth factors, and any combinations thereof. Suitable polysaccharides would include starch, glycogen, cellulose, pectin, amylase, dextrin, polysucrose or chitosan. With reference to suitable growth factors for chemical couplings with the peptides of the present invention, these include, but are not limited to, bFGF, GCSF, an ILGF-1, or VEGF. In addition, the peptides of the invention may be conjugated to a synthetic polymer, e.g. polyethylene glycol or polyvinyl alcohol, to phospholipids including ceramics or paraffin and to alcohols, such as glycerol.

The chemical coupling between the peptides of the invention and any one of the class substances described above is generally affected directly via reactive groups of the carrier substance and the peptide or with the aid of the linkers. For example, the bi-functional linker sulphosuccinimidyl-4-(N-maleimidomethyl)-cyclohexane-1-carboxylate may be used to couple peptides of the invention to a suitable growth factor or extracellular matrix protein. Reactive groups may be already present on the carrier and the peptide. However, they can also be introduced by activating a reactive group in the molecule. Common reactive functionalities include amino, imino, hydroxyl, sulphohydryl or carboxyl groups.

It is noted that it may be advantageous to conjugate more than one peptide molecule to a particular carrier in order to facilitate enhanced adhesion and growth promoting properties.

In one embodiment of the invention, the carrier member of the conjugate is adsorbed to a particular surface, such as a tissue culture surface. For example, the carrier may be an extracellular matrix protein adsorbed to the surface and contained a reactive functionality to provide for binding or conjugation to a peptide or peptides of the invention, such as by reaction with a non-natural amino acid at either the N-terminus or C-terminus of the peptides. In this instance, the modified peptide is added to a tissue culture substrate which has already been precoated with a carrier containing a reactive functionality. Alternatively, a preformed conjugate is added to a culture system, either by coating of the conjugate on a surface or by inclusion of the conjugate as a media component.

As described above, several of the peptides of the present invention are useful for enhancing adherence of cells to a surface and to enhance cellular growth thereon, as measured by increased oxygen consumption of the cells when compared with adherence and growth on uncoated surfaces. To this end, the present invention provides a cell culture substrate including one or more of the peptides corresponding to SEQ ID NO:1 through SEQ ID NO:11.

Alternatively, a substrate may be coated with a peptide composition including one or more of the following pairs of peptides (a) SEQ ID NO:12/SEQ ID NO:13 and (b) SEQ ID NO:14/SEQ ID NO:15, which as already described enhance adherence and growth of anchorage-dependent cells.

The invention also provides a cell culture substrate including a peptide selected from the secretion-enhancing peptides corresponding to SEQ ID NO:16 through SEQ ID NO:70 and SEQ ID NO:5 and combinations thereof.

It is well within the contemplation of the present invention that the cell/tissue culture substrate may, in an addition to including a peptide of the present invention, further include at least one of the following: bovine serum albumin, keyhole limpet haemocyanin, collagen, fibronectin, laminin, polylysine, a peptide having a cell-surface receptor recognition sequence, an immunoglobulin, a polysaccharide, or a growth factor. For example, a peptide according to the present invention may synergize with a protein present on the surface to allow for enhanced adhesion of anchorage-dependent cells and enhanced cellular growth. The invention further contemplates that the cell culture substrate may include a monolayer of cells.

The peptide suitable for coating of a substrate may be covalently linked to a carrier such as those described above which included extracellular matrix proteins, bovine serum albumin, polylysine, an immunoglobulin, polysaccharide, or a growth factor among others. As described above, the peptide may be conjugated to a carrier followed by coating of the conjugate on the surface or, alternatively, the peptide is conjugated or covalently linked to a carrier which has been precoated on the surface, provided that suitable reactive functionalities are present on the peptide, carrier, and molecular linker, when present.

The present invention provides a peptide library selected from the following libraries: (a) xxxkx, (b) xxkxx, (c) xxxxk, (d) xkxxx, (e) kxxxx and permutations thereof, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof.

In one embodiment, the peptide library of the present invention includes peptides which are covalently linked to a particular carrier. Suitable carriers are the same as those described above and include, but are not limited to, bovine serum albumin, keyhole limpet haemocyanin, collagen, fibronectin, laminin, polylysine, a peptide having a cell-surface receptor recognition sequence, an immunoglobulin, a polysaccharide, and a growth factor.

With reference to methods provided by the present invention, a method is provided for modifying a surface in a cell culture system so as to enhance cell growth and/or secretion in the system, wherein the method includes the step of applying to this surface a peptide including a structure selected from the following group: (a) xxxkx, (b) xxkxx, (c)

xxxxk, (d) xkxxx, (e) kxxxx and combinations thereof, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine and derivatives thereof.

Specific peptides suitable for use in modifying a surface to as to promote cell adherence and growth thereon include those selected from the following: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11 and combinations thereof.

Moreover, one or more of the following inventive peptide compositions are suitable for modifying a surface so as to promote cell adherence and growth thereon: (a) SEQ ID NO:12/SEQ ID NO:13 and (b) SEQ ID NO:14/SEQ ID NO:15.

In a further embodiment, one or more of the peptides corresponding to SEQ ID NO:16 through SEQ ID NO:56 and SEQ ID NO: 5 may be applied to a substrate in a cell culture system so as to enhance cell secretion.

Further provided by the present invention is a method of adhering cells to a surface to promote cellular growth including the steps of (i) providing a surface at least partially coated with a peptide including a structure selected from the following: (a) xxxkx, (b) xxkxx, (c) xxxxk, (d) xkxxx, (e) kxxxx and combinations thereof, wherein k represents lysine and each x may be the same or different hydrophobic or uncharged polar amino acid and (ii) contacting the at least partially coated surface with the cells for a sufficient time to permit cellular attachment thereto. In one embodiment, the hydrophobic or uncharged polar amino acid residue is selected from the following: Phe, Ile, Ala, Val, Pro, Gly, Gln and derivatives thereof.

Specific peptides suitable for use in adhering anchorage-dependent cells to a surface to promote cellular growth include the sequences represented by Sequence ID NO: 1 through Sequence ID NO: 11 and combinations thereof. Moreover, the inventive compositions corresponding to the following peptide pairs are useful: (SEQ ID NO:12/SEQ ID NO:13) AND (SEQ ID NO:14/SEQ ID NO:15). The peptides may be covalently linked to any one of the carriers described above.

In one embodiment of the method of adhering cells to a surface to promote cellular growth, the cellular growth occurs in vitro, such as on a tissue culture substrate including, but not limited to, microtitre wells, tissue culture flasks, dishes, and bottles. Alternatively, cellular growth may occur in vivo such as on a biomedical device which is implanted in a body.

With respect to the use of the inventive peptides in biomedical implants, it is generally desirable that the surrounding cells in the tissues adhere to and spread upon the implant surface. The peptides of the present invention provide a means for surface modification to obtain such a desired implant integration within the host. In particular, the surface-treated biomedical implant devices enhance the amount and rate of cell adhesions to the surface, as well as growth and therefore the rate of tissue integration of the device in vivo. Moreover, the enhanced adherence and growth of the cells provides a continuous protective layer between the biomedical device and the biological tissue to prevent entry of bacteria and other infectious agents into the tissue. With an enhanced cell adhesion promoting surface included as a part of the device, the undesirable effect would be minimized since the protective cell covering reduces the opportunity for potential entry of infectious agents.

Moreover, the peptides of the present invention have the desirable property of reduced susceptibility to cellular proteases which lends long-term stability to the disclosed treated surfaces. This makes the method of modifying surfaces with peptides of the present invention an ideal system in preparing various biomedical implants for extended term body emplacement. These would include, but not be limited to, nerve growth guides and indwelling catheters. The method of modifying surfaces using the system of the present invention would also be useful in the design of a mammalian cell bioreactor, since it provides a stable integral surface component which allows for support of cell adhesion and cell growth without the absolute requirement of medial cell adhesion molecules such as fibronectin and collagen. Furthermore, a substrate coated with the peptide of the invention provides the further advantage of allowing the use of low serum or serum-free media which is low or deficient in cell adhesion molecules.

The method for modifying surfaces with peptides of the present invention may be useful in the treatment of laboratory glassware and plasticware used as cell culture substrates, including, but not limited to, tissue-culture flasks and petri dishes. With reference to large scale tissue and cell culture, the method may be useful in treating surfaces of microcarriers, macrocarriers, hollow fibers, and roller bottles. Moreover, the method may be useful for treatment of the interior of an implantable artificial vascular graft in order to promote endothelialization of the surfaces. Moreover, exterior and end regions of vascular grafts may be treated with peptides of the present invention to promote integration into the tissues. The peptides of the present invention may also be useful for other implantable devices such as artificial tendons, ligaments, bone screws and plates, bone fragments, joints, and skin where integration of the implantable device with the tissues is desirable. Furthermore, sutures may be treated to promote adhesion with an integrating tissue.

Peptide Affecting Cell Adherence and Growth

EXAMPLE 1

Cell Line

MC3T3-E1 is a clonal line of murine calvaria-derived osteoblast (establishement of a clonal osteogenic Cell Line from Newborn Mouse Calvaria in Jpn J. Oral Biol 23, 899 (1981)).

EXAMPLE 2

Cell Maintenance

MC3T3 cells were maintained in αMEM (GIBCO Catalog No: 12561) supplemented with 2% fetal calf serum (FCS, inactivated) and 100 units or μg/ml of penicillin/streptomycin for one month prior to use. Cells were routinely seeded at a density of approximately $1 \times 10^4$ cells per 20 ml culture media which was placed in a 250 ml canted neck polystyrene tissue culture treated flask (Becton Dickinson). Cells were cultured until approximately $2 \times 10^6$ cells were obtainable from each flask, which were resuspended in 5 ml of αMEM with 2% FCS for a final cell concentration of about $5 \times 10^4$ cells per 150 μl for peptide screening.

EXAMPLE 3

Screening Conditions

For determining the biological effects of library peptides and appropriate controls on MC3T3 cells, cells ($5\times10^4$/150 µl) were grown in an 96 well oxygen sensor plate treated as described below:

Library Peptides

Peptides for screening were obtained from either a MDL-400 library or an MDL-100 library. Fifty microliters of peptides at a 1 mM stock concentration in phosphate buffered saline were placed in wells of a 96 well oxygen sensor plate and dried in a reverse flow air hood overnight for 30 hours.

Controls

Vitrogen-collagen-I was obtained from Cohesion (Palo Alto, Calif., Catalog No. FXP-019) and fibronectin was obtained from Sigma (Catalog No. F-0895). All other extracellular matrix (ECM) compounds were obtained from Becton Dickinson Labware, (Bedford, Mass.). Polylysine was obtained from Becton Dickinson Labware and RGDSP-rhodamine was from AnaSpec Inc. (San Jose, Calif.). Extracellular matrix components (ECM) or known peptides were used at the following stock concentrations:

| | |
|---|---|
| Vitrogen-Collagen-I | 3.2 mg/ml |
| Fibronectin | 0.1% |
| Collagen-V | 1 mg/ml |
| Laminin | 2 mg/ml |
| h-Collagen-I | 1 mg/ml |
| Collagen-IV | 0.5 mg/ml |
| Collagen-III | 1 mg/ml |
| Polylysine | 5 mg/ml |
| RGDSP-rhodamine | 1 mg/ml |

Twenty-five micro liters of stock concentrations of controls and 25 µl of phosphate buffered saline were placed in wells of a 96 well oxygen sensor plate and dried overnight as described above.

EXAMPLE 4

Monitoring of Cell Growth

Cells grown on 96 well oxygen sensor plates treated as described above were monitored for growth using a Becton Dickinson oxygen biosensor. Growth was monitored at the following time points: 1 hours, 24 hours, 32 hours, 48 hours and 86 hours. Media was changed every three days. Media was not supplemented with additional peptide during culturing.

The fluorescent oxygen biosensor assay allowed for real time noninvasive monitoring of cellular growth. The assay is based upon measurement of oxygen dissolved in assay mediums. The Becton Dickinson biosensor is based upon the fluorescence of ruthenium dye that is quenched in the presence of oxygen. The dye is immobilized within an inert but highly oxygen-permeable silicone matrix. Previous data suggested that increase in cell number correlates well with increase in oxygen consumption.

All data was obtained with a polarstar fluorimeter (BMG Lab Technologies, Durham, N.C.) at 37 C using the bottom plate reading configuration. The band-pass filters were 465 nm for excitation and 590 nm for emission. Because the intensity readouts on fluorescence plates are in arbitrary units, values were normalized by dividing well values at selected time points by the same well's initial reading, prior to adding cells. (Wodnicka, M., Guarino, R. D., Hemperly, J. J. Temmins, M. R., Stitt, D. and Pitner, J. B. (2000) J. of Biomolecular Screening 5:141–152)

EXAMPLE 5

Results of Oxygen Biosensor Assays

The data presented in this example demonstrates that the inventive peptides effectively promote the adherence and growth of anchorage-dependent MC3T3 cells on tissue culture surfaces and that these effects are similar to those obtained from known ECM components. As described above, library peptides and controls are adsorbed to the bottom of the wells of an oxygen biosensor multiwell plate prior to the addition of cells. Growth is monitored with an oxygen biosensor assay as described above. The absorbance readout at 590 nm provides a measure of relative oxygen consumption of the cells which correlates with cell growth. Growth of the cells was compared in presence and absence of peptides from a peptide library (MDL-400 and MDL-100). Growth was further compared with ECM controls and known peptide controls as described in further detail below.

The criteria for selection of the inventive peptides was a relative oxygen consumption (Absorbance at 590 nm) of 2.0 and above at the 86 hour time point. As shown in Tables 1 and 2 below, a total of eleven inventive peptides were identified in the MDL-400 library as having an absorbance of 2.0 or greater. Referring to Table 2, these peptides correspond to SEQ ID NO:1–SEQ ID NO:11.

With further reference to Tables 1 and 2, two inventive peptide compositions were identified in the MDL-100 library as having an absorbance greater than 2.0. The compositions correspond to the following peptide pairs: (SEQ ID NO:12/SEQ ID NO:13) and (SEQ ID NO:14/SEQ ID NO:15) as indicated in Table 2.

It is noted that the results for controls and peptides shown in Table 1 were obtained from the same 96 well oxygen sensor plate at the 86 hour time point. It is further noted that similar absorbance patterns were obtained at earlier time points, with inventive peptides and peptide compositions giving higher absorbance readings relative to other library peptides on the same assay plate. However, overall absorbance values were less than those obtained at 86 hours, as would be expected.

TABLE 1

| MDL-400 Library | | MDL-100 Library | | Controls | |
|---|---|---|---|---|---|
| Peptide No. | Abs at 590 nm | Peptide Nos. | Abs at 590 nm | Condition | Abs at 590 nm |
| 592 | 2.11* | 5, 6 | 1.27 | Vitrogen-Collagen-I | 1.26 |
| 596 | 1.65 | 7, 11 | 1.22 | Collagen-IV | 3.14 |
| 601 | 2.38* | 12, 15 | 1.38 | Fibronectin | 2.12 |
| 593 | 1.42 | 18, 19 | 1.50 | Collagen-III | 1.45 |
| 597 | 2.08* | 24, 26 | 1.55 | Collagen-V | 1.76 |
| 524 | 1.71 | 27, 31 | 1.70 | h Collagen-I | 1.79 |
| 528 | 1.45 | 33, 36 | 1.38 | Laminin | 2.65 |
| 530 | 1.77 | 40, 42 | 1.39 | Polylysine | 1.08 |
| 531 | 1.70 | 46, 48 | 1.60 | RGDSP | 1.25 |
| 590 | 2.06* | 53, 60 | 1.63 | HECM | 1.78 |
| 533 | 1.30 | 61, 66 | 2.22* | Serum | 1.35 |
| 535 | 1.57 | 67, 70 | 1.40 | Cells & media | 1.20 |
| 536 | 1.81 | 72, 74 | 1.62 | Media | 1.15 |
| 538 | 1.81 | 75, 76 | 1.31 | | |
| 594 | 1.50 | 77, 78 | 1.46 | | |

TABLE 1-continued

| MDL-400 Library | | MDL-100 Library | | Controls | |
|---|---|---|---|---|---|
| Peptide No. | Abs at 590 nm | Peptide Nos. | Abs at 590 nm | Condition | Abs at 590 nm |
| 539 | 1.48 | 83, 84 | 1.91 | | |
| 540 | 1.68 | 85, 87 | 1.93 | | |
| 541 | 1.29 | 99, 102 | 1.89 | | |
| 544 | 2.11* | 106, 123 | 1.28 | | |
| 599 | 1.81 | 128, 133 | 1.98 | | |
| 549 | 1.60 | 138, 141 | 2.13* | | |
| 575 | 1.29 | 144, 145 | 1.37 | | |
| 576 | 1.55 | 149, 151 | 1.90 | | |
| 577 | 1.87 | 161, 163 | 1.77 | | |
| 591 | 2.53* | | | | |
| 579 | 1.31 | | | | |
| 583 | 1.33 | | | | |
| 584 | 2.27* | | | | |
| 585 | 2.01* | | | | |
| 595 | 2.06* | | | | |
| 586 | 1.78 | | | | |
| 587 | 1.56 | | | | |
| 588 | 2.08* | | | | |
| 589 | 2.78* | | | | |
| 600 | 1.93 | | | | |

*denotes inventive peptides/peptide compositions

TABLE 2

| Inventive Peptide No. | Identity |
|---|---|
| 61, 66 | SEQ ID NO:12/SEQ ID NO:13 |
| 138, 141 | SEQ ID NO:14/SEQ ID NO:15 |
| 592 | SEQ ID NO:10 |
| 601 | SEQ ID NO:2 |
| 597 | SEQ ID NO:3 |
| 590 | SEQ ID NO:11 |
| 544 | SEQ ID NO:4 |
| 591 | SEQ ID NO:1 |
| 584 | SEQ ID NO:5 |
| 585 | SEQ ID NO:6 |
| 595 | SEQ ID NO:7 |
| 588 | SEQ ID NO:8 |
| 589 | SEQ ID NO:9 |

A graph of the results in Table 1 which were obtained at the 86 hour time point from the oxygen biosensor assay is shown in FIG. 1, where the inventive peptides are compared with ECM or known peptide controls. As shown, the inventive peptides promote the growth of MC3T3 cells wherein the peptide controls, polylysine and RGDSP, do not. These peptide controls are known to promote cellular attachment to tissue culture substrates, which is a prerequisite for the growth of anchorage-dependent cell in vitro (Grinnel, F. Psychology, 53:67–149, 1978 and Couchman et al., J. Cell Biol., 93:402–410, 1982).

Furthermore, the graph in FIG. 1 indicates that each of the inventive peptides was better at promoting adherence and growth of MC3T3 cells then several of the ECM controls including Vitrogen-Collagen-I, Collagen-III, Collagen-V, h-Collagen-I, HECM and serum.

Moreover, each of the inventive peptides was equal to or better than the fibronectin control at promoting adherence and growth of the cells. Lastly, the performance of two of the inventive peptides, SEQ ID NO:1 and SEQ ID NO:9, which showed relative oxygen consumptions of 2.53 and 2.78, respectively, performed comparably to the Collagen-IV and Laminin controls which gave absorbance of 3.14 and 2.65, respectively.

Peptides Affecting Secretion of PDGF

EXAMPLE 6

Cell Line

Chinese Hamster Ovary (CHO) Cells possessing a gene for PDGF were selected for secretion screens. CHO cells are the most widely used animal cell lines in the field of biotechnology for the production of therapeutically important pharmaceuticals (Martin et al, REVIEW, J. of Biotechnology. Progress 1998 14, 807–833). The Chinese Hamster Ovary Cell Lines producing rPDGF (CRL 9359/CRL9360) were obtained from the American Type Culture Collection, 12301 Parklawn Drive, Rockville, Md. 20852. The depositor was Amgen Inc. of Thousand Oaks, Calif. Further details about the cell lines and expressed products can be found in U.S. Pat. No. 5,175,255.

EXAMPLE 7

Cell Maintenance

Cells were propagated in DMEM/F12 media with 5% serum at 37° C. between 5–7% $CO_2$. Passages were limited to 5 prior to seeding and PDGF expression was monitored by western blot and ELISA. Cells were routinely seeded at a density of approximately $1 \times 10^4$ cells per 20 ml culture media that was placed in a 250 ml canted neck polystyrene tissue culture treated flask (Becton Dickinson). Cells were cultured to confluency and trypsinized to yield cells for seeding.

EXAMPLE 8

Preparation of Supplement-Rich 1A Media and Controls

1A Media was used as a PDGF negative control (pre-culture), to hydrate the 40 ng PDGF standard (pre-culture), to hydrate test peptides (pre-culture) and to normalize all other test and control PDGF results (post-culture). The 1A media was prepared by adding the following components to a 500 ml bottle of DMEM/F12 (GIBCO cat. No. 11330-032): 2.5 ml of a 10 mM NEAA stock (GIBCO Catalog 11140-050); 10 ml of a 200 mM L-glutamine stock (GIBCO Catalog 25030-08); 1 ml of a 50 mg/ml gentamycin sulfate stock (GIBCO Catalog 15750-0601); 150 µl of a 100 µM methotrexate Stock (Sigma Catalog M8407); 0.5 ml of a 7.5 mg/ml insulin Stock (Sigma I-6634); 50 µl of a 1 mg/ml insulin-like growth factor-stock (Long R3 Factor, Sigma Catalog No. I-1271); 2.5 grams of bovine serum albumin (Sigma Catalog No. A-7906); and 0.5 ml of a 7.5 mg/ml holo-transferrin stock (Sigma T-1283).

EXAMPLE 9

Culture Plate Set-Up and Sampling

The CHO model cell lines are adherent cultures that have never been adapted to a serum-free environment. Accordingly, media containing serum was used to seed wells. Two formats, Overlay (O) and Wash (W) were used to introduce media containing test peptides to adhered cells.

In the O-Format, compounds were gently added on top of the seeding media on the second day. In the O-Format, 9360 cells were seeded at 1,000 cells per 96 well in a 125 µl volume of 1A media with 1.5% serum. 1A media (-serum) containing 12 mM of test peptide was overlaid 2 days later for a final peptide concentration of 6 mM and 0.75% serum. Cell culture supernatant was collected from each test environment on day 10 for later PDGF assay.

In the W-Format, compounds were added on day 2 or 3 after the seeding media was removed. In the W-Format, 9359 and 9360 cells were seeded at 6,000 cells per 96 well in a 250 µl volume of DMEM/F12 with 5% serum. Three days later, the seeding media was removed and replaced with 250 µl of 1A media (-serum) containing 6 mM test peptide. Cell culture supernatant was collected on days 5 and 12 for later PDGF assay.

EXAMPLE 10

Monitoring PDGF in Tissue Culture Supernatant

Supernatant was collected from each culture of CRL9359/9360 propagated in a media containing test compound. The rPDGF levels were measured by the ELISA which will now be described.

Plates were coated with mouse anti-human PDGF AB/BB subunits (IgG1) obtained from PharMingen (Catalog No. 15-681A) for 1 hour at 37° C., followed by decantation of the antibody solution. Blocking agent was then added followed by incubation at 37° C. for an hour to eliminate non-specific binding. The blocking agent was decanted and the plates were washed three times. Test supernatant along with positive and negative controls (Positive control= Pool of Sigma Human rPDGF Catalog Nos: P3201 and P4306 or P3201 alone) were then added and incubated for one hour at 37° C. The solution was then decanted and the plates were washed three times. Antibody specific to PDGF of the IgG2a isotype was next added (Amgen MAB 133 obtained from ATCC) and incubation was for one hour at 37° C. Following decantation of the antibody solution, the plates were washed. Secondary antibody HRP conjugate anti-mouse (IgG2a specific) was then added and incubated for one hour at 37° C. After decanting the secondary antibody solution, the plates were again washed. The substrate for the peroxidase was then added and the color was allowed to develop. The reaction was then stopped and plates were read at 492 nm.

Signals from the inventive peptides were at least 0.2 OD higher than the 1A base media (rich with traditional supplements). Data was only accepted if the base media (pre-culture) was less than 0.2 OD (raw value) and the spread between the 1A base media (post culture) and 40 ng PDGF standard was 0.5 OD.

EXAMPLE 11

Results of PDGF Assays

The data presented in this example demonstrates that the inventive peptides effectively promote the expression and secretion of PDGF in anchorage-dependent CHO cells on tissue culture surfaces and that these effects are beyond the results achieved with a media containing serum and/or a pool of common serum supplements. As described above, library peptides and controls are added to a 96-well plate after cells are adhered. Accumulation of PDGF in the superntant was monitored by a sandwich ELISA. The absorbance readout at 492 nm provides a measure of relative PDGF levels stimulated by each test peptide. Supernatant PDGF levels were compared in the presence and absence of peptides from several peptide libraries. PDGF levels were further compared with media; pre-culture, post-culture and pre-culture spiked with a known concentration of PDGF.

The criteria for selection of the inventive peptides was a relative ELISA PDGF value (Absorbance at 492 nm) minimally 0.2 over the 1A base media at day 12 or sooner. As shown in Table 3 below, a total of fifty-six inventive peptides were identified in the combined MDL-100/400 and follow-up libraries. These peptides correspond to SEQ ID NO:16-SEQ ID NO:70 plus SEQ ID NO:5 that was also positive for MC3T3 growth.

Table 3 below contains results obtained from controls in a typical Enzyme Linked immunoabsorbant Assay for Platelet Derived Growth Factor. Raw and normalized values are shown for assay controls, 1A media pre-culture, 1A media post-culture and 1A media pre-culture spiked to 40 ng/ml with PDGF.

Table 3 contains results obtained from multiple Enzyme Linked Immunoabsorbant Assays for Platelet Derived Growth Factor. Inventive pentamers were identified in an initial maximum diversity library (MDL-100), a follow-up library comprised of compounds filling in the property space (MDL-400) and a follow-up library around early leads. Biological effects on the cells, above the base media (1A) are shown as the values for inventive peptides were normalized versus 1A media (where the 1A media value post culture was subtracted). The absorbance at 492 nm is a measure of relative PDGF levels in the cell culture supernatant of the inventive pentamers. It is noted that 42 of 51 pentamers contained the basic amino acid, lysine. Three examples of negative peptides found in MDL-100, MDL-400 and follow-up screens are shown in Table 3.

Table 3 follow-up library includes results obtained from commercially available diamers, trimers and tetramers containing lysine; SEQ ID NO:68, SEQ ID NO:67 and SEQ ID NO:66, respectively. Values for trimers of arginine and the arginine precursor, ornithine; SEQ ID NO:70 and SEQ ID NO:69 are also provided in the follow-up library column. These results demonstrate that peptides comprised in their entirety of lysine or arginine or the arginine percursor ornithine have a positive effect on PDGF accumulation in the media.

TABLE 3

| MDL-400 Library | | MDL-100 Library | | Follow-Up Library | |
|---|---|---|---|---|---|
| Inventive Peptide Seq. ID No. | Normalized Abs at 492 nm | Inventive Peptide Seq. ID No. | Normalized Abs at 492 nm | Inventive Peptide Seq. ID No. | Normalized Abs at 492 nm |
| 16 | 1.38 | 17 | 1.32 | 18 | 0.82 |
| 19 | 0.79 | 33 | 0.44 | 5 | 0.77 |
| 22 | 0.59 | 47 | 0.28 | 20 | 0.76 |

TABLE 3-continued

| MDL-400 Library | | MDL-100 Library | | Follow-Up Library | |
|---|---|---|---|---|---|
| Inventive Peptide Seq. ID No. | Normalized Abs at 492 nm | Inventive Peptide Seq. ID No. | Normalized Abs at 492 nm | Inventive Peptide Seq. ID No. | Normalized Abs at 492 nm |
| 27 | 0.55 | 49 | 0.26 | 21 | 0.64 |
| 30 | 0.50 | 59 | 0.55 | 23 | 0.58 |
| 31 | 0.49 | 62 | 0.34 | 24 | 0.58 |
| 34 | 0.42 | 64 | 0.26 | 25 | 0.58 |
| 37 | 0.38 | | | 26 | 0.56 |
| 38 | 0.37 | | | 28 | 0.55 |
| 43 | 0.32 | | | 29 | 0.51 |
| 44 | 0.31 | | | 32 | 0.48 |
| 46 | 0.28 | | | 35 | 0.42 |
| 50 | 0.25 | | | 36 | 0.39 |
| 51 | 0.25 | | | 39 | 0.37 |
| 53 | 0.22 | | | 40 | 0.36 |
| 56 | 0.20 | | | 41 | 0.36 |
| 58 | 0.58 | | | 42 | 0.35 |
| 60 | 0.45 | | | 45 | 0.28 |
| 61 | 0.43 | | | 48 | 0.26 |
| 63 | 0.33 | | | 52 | 0.25 |
| 65 | 0.23 | | | 54 | 0.22 |
| | | | | 55 | 0.21 |
| | | | | 57 | 0.68 |
| | | | | 66 | 1.37 |
| | | | | 67 | 1.11 |
| | | | | 68 | 0.34 |
| | | | | 69 | 1.31 |
| | | | | 70 | 0.90 |
| Negative Peptide | | Negative Peptide | | Negative Peptide | |
| | −0.41 | | −0.36 | | −0.21 |
| | −0.05 | | −0.81 | | −0.56 |
| | −0.23 | | −1.07 | | −0.64 |

| Controls | Raw Value | Normalized |
|---|---|---|
| Base Media, Pre Culture | 0.20 | −1.08 |
| Base Media, Post Culture | 1.28 | 0.00 |
| 40 ng PDGF Std. | 2.47 | 1.19 |

---

What is claimed is:

1. A cell culture system comprising a pentameric peptide which enhances cell growth and/or secretion, wherein said peptide comprises a pentameric structure of at least one of (a) xxxkx, (b) xxkxx, (c) xxxxk, (d) xkxxx, and (e) kxxxx, wherein k represents lysine and each x may be the same or different amino acid independently selected from the group consisting of lysine, alanine, isoleucine, phenylalanine, proline, valine, glycine, glutamine, leucine, methionine, asparagine, serine, threonine, tyrosine, aspartic acid, glutamic acid, histidine, and derivatives thereof, and wherein said peptide is covalently linked to a growth factor, wherein said growth factor comprises at least one of bFGF, GCSF, an ILGF-1, or VEGF.

2. The system of claim 1, wherein the peptide promotes adherence of anchorage-dependent cells on a surface.

3. The system of claim 1, wherein the peptide enhances cell growth and is selected from the group consisting of IFFKG (SEQ ID NO:1), FIKFG (SEQ ID NO:2), FIFAK (SEQ ID NO:3), QVVAK (SEQ ID NO:4), FKFIG (SEQ ID NO:5), AFFKI (SEQ ID NO:6), VFPFK (SEQ ID NO:7), AKIFF (SEQ ID NO:8), AFKIF(SEQ ID NO:9), KFAFI (SEQ ID NO:10), FAKFI (SEQ ID NO:11), and combinations thereof.

4. The system of claim 1, wherein the peptide enhances cell secretion and is selected from the group consisting of FKLVY (SEQ ID NO:16), KKKKK (SEQ ID NO:17), KKKKL (SEQ ID NO:18), FKKKQ (SEQ ID NO:19), FKFIG (SEQ ID NO:5), KKKSK (SEQ ID NO:20), KKKLK (SEQ ID NO:2 1), FKKKK (SEQ ID NO:22), LKKKK (SEQ ID NO:23), KKLKK (SEQ ID NO:24), KKKKT (SEQ ID NO:25), KKPKK (SEQ ID NO:26), KKPQY (SEQ ID NO:27), SKKKK (SEQ ID NO:28), KVKKK (SEQ ID NO:29), KNQTY (SEQ ID NO:30), FKKKV (SEQ ID NO:31), KPKKK (SEQ ID NO:32), FFKKK (SEQ ID NO:33), HKNQT (SEQ ID NO:34), FKLVG (SEQ ID NO:35), KKQPK (SEQ ID NO:36), EKKQT (SEQ ID NO:37), EKKKK (SEQ ID NO:38), KKIKQ (SEQ ID NO:39), KKKKS (SEQ ID NO:40), KKQKK (SEQ ID NO:41), KKLNY (SEQ ID NO:42), DGKKT (SEQ ID NO:43), KKPTT (SEQ ID NO:44), KFIFG (SEQ ID NO:45), FKKMY (SEQ ID NO:46), FFFKK (SEQ ID NO:47), KQKKI (SEQ ID NO:48), HIKKK (SEQ ID NO:49), DFFHK (SEQ ID NO:50), AKKKK (SEQ ID NO:51), AHIKK (SEQ ID NO:52), AHKKK (SEQ ID NO:53), LKLVY (SEQ ID NO:54), PKQKK (SEQ ID NO:55), AKKKT (SEQ ID NO:56), and combinations thereof.

5. The system of claim 1, wherein said peptide is introduced into the cell culture system at a concentration of about 500 µM to about 6 mM.

6. The system of claim 1, wherein said peptide is introduced into the cell culture system at a concentration of about 250 µM to about 24 mM.

7. The system of claim 1, wherein said peptide is introduced into the cell culture system at a concentration ranging from 3 mM to about 12 mM.

8. A cell culture system comprising a pentameric peptide which enhances cell growth and/or secretion, wherein said peptide is HKNQT (SEQ ID NO:34), and wherein said peptide is present on a surface in the form of a dried film.

9. The system of claim 8, wherein said surface is two dimensional or three dimensional.

10. The system of claim 8, wherein the cell culture system comprises cells selected from the group consisting of epithelial, endothelial, dermal, neural, tumor, lymphocytic, stem cells, and combinations thereof.

11. The system of claim 10, wherein said peptide increases oxygen consumption of said cells.

12. The system of claim 10, wherein said peptide enhances growth of said cells in vitro or in vivo.

13. The system of claim 8, wherein the peptide is non-covalently attached or nonspecifically adsorbed to the surface.

14. The system of claim 13 wherein said surface is coated with at least one of bovine serum albumin, ovalbumin, keyhole limpet haemocyanin, collagen, fibronectin, laminin, polylysine, a peptide having a cell-surface receptor recognition sequence, an immunoglobulin, a polysaccharide, or a growth factor.

15. The system of claim 13 wherein said surface is selected from the group consisting of plastic dishes, plastic flasks, plastic microtitre plates, plastic tubes, sutures, membranes, films, bioreactors, hollow fibers, sacs and microparticles.

16. The system of claim 8, wherein the peptide is covalently linked to a member of the group consisting of extracellular matrix protein, bovine serum albumin, ovalbumin, keyhole limpet haemocyanin, collagen, fibronectin, laminin, an immunoglobulin, a polysaccharide, a growth factor, and combinations thereof.

17. The system of claim 16, wherein said member is adsorbed to a surface.

18. The system of claim 16, wherein said growth factor comprises at least one of bFGF, GCSF, an ILGF-1, or VEGF.

19. The system of claim 1, wherein the peptide is a media constituent.

20. A peptide which enhances cell secretion comprising HKNQT (SEQ ID NO:34), wherein said peptide is attached or nonspecifically adsorbed to a surface.

21. A method of modifying a surface in a cell culture system so as to enhance cell growth and/or secretion in said system, comprising the step of noncovalently attaching or nonspecifically adsorbing to said surface a pentameric peptide comprising HKNQT.

22. The method of claim 21, wherein the peptide enhances cell secretion.

23. A cell or tissue culture medium comprising HKNQT (SEQ ID NO: 34).

24. A method for enhancing cellular growth and/or secretion comprising the step of culturing cells or tissues in the presence of HKNQT (SEQ ID NO: 34).

25. The system of claim 1, wherein said peptide is present on a surface in the form of a dried film.

26. The system of claim 25, wherein said surface is two dimensional or three dimensional.

27. The system of claim 1, wherein the cell culture system comprises cells selected from the group consisting of epithelial, endothelial, dermal, neural, tumor, lymphocytic, stem cells, and combinations thereof.

28. The system of claim 27, wherein said peptide increases oxygen consumption of said cells.

29. The system of claim 27, wherein said peptide enhances growth of said cells in vitro or in vivo.

30. The system of claim 1, wherein the peptide is noncovalently attached or nonspecifically adsorbed to a surface.

31. The system of claim 30, wherein said surface is coated with at least one of bovine serum albumin, ovalbumin, keyhole limpet haemocyanin, collagen, fibronectin, laminin, polylysine, a peptide having a cell-surface receptor recognition sequence, an immunoglobulin, a polysaceharide, or a growth factor.

32. The system of claim 30, wherein said surface is selected from the group consisting of plastic dishes, plastic flasks, plastic microtitre plates, plastic tubes, sutures, membranes, films, bioreactors, hollow fibers, sacs, and microparticles.

33. The system of claim 1, wherein said peptide comprises a pentameric structure of xxxkx.

34. The system of claim 1, wherein said peptide comprises a pentameric structure of xxkxx.

35. The system of claim 1, wherein said peptide comprises a pentameric structure of xxxxk.

36. The system of claim 1, wherein said peptide comprises a pentameric structure of xkxxx.

37. The system of claim 1, wherein said peptide comprises a pentameric structure of kxxxx.

38. The system of claim 3, wherein said peptide is IFFKG (SEQ ID NO:1).

39. The system of claim 3, wherein said peptide is IFKFG (SEQ ID NO:2).

40. The system of claim 3, wherein said peptide is FIFAK (SEQ ID NO:3).

41. The system of claim 3, wherein said peptide is QVVAK (SEQ ID NO:4).

42. The system of claim 3, wherein said peptide is FKFIG (SEQ ID NO:5).

43. The system of claim 3, wherein said peptide is AFFKI (SEQ ID NO:6).

44. The system of claim 3, wherein said peptide is VFPFK (SEQ ID NO:7).

45. The system of claim 3, wherein said peptide is AKIFF (SEQ ID NO:8).

46. The system of claim 3, wherein said peptide is AFKIF (SEQ ID NO:9).

47. The system of claim 3, wherein said peptide is KFAFI (SEQ ID NO:10).

48. The system of claim 3, wherein said peptide is FAKFI (SEQ ID NO:11).

49. The system of claim 4, wherein said peptide is FKLVY (SEQ ID NO:16).

50. The system of claim 4, wherein said peptide is KKKKK (SEQ ID NO:17).

51. The system of claim 4, wherein said peptide is KKKKL (SEQ ID NO:18).

52. The system of claim 4, wherein said peptide is FKKKQ (SEQ ID NO:19).

53. The system of claim 4, wherein said peptide is FKFIG (SEQ ID NO:5).

54. The system of claim 4, wherein said peptide is KKKSK (SEQ ID NO:20).

55. The system of claim 4, wherein said peptide is KKKLK (SEQ ID NO:21).

56. The system of claim 4, wherein said peptide is FKKKK (SEQ ID NO:22).

57. The system of claim 4, wherein said peptide is LKKKK (SEQ ID NO:23).

58. The system of claim 4, wherein said peptide is KKLKK (SEQ ID NO:24).

59. The system of claim 4, wherein said peptide is KKKKT (SEQ ID NO:25).

60. The system of claim 4, wherein said peptide is KKPKK (SEQ ID NO:26).

61. The system of claim 4, wherein said peptide is KKPQY (SEQ ID NO:27).

62. The system of claim 4, wherein said peptide is SKKKK (SEQ ID NO:28).

63. The system of claim 4, wherein said peptide is KVKKK (SEQ ID NO:29).

64. The system of claim 4, wherein said peptide is KNQTY (SEQ ID NO:30).

65. The system of claim 4, wherein said peptide is FKKKV (SEQ ID NO:31).

66. The system of claim 4, wherein said peptide is KPKKK (SEQ ID NO:32).

67. The system of claim 4, wherein said peptide is FFKKK (SEQ ID NO:33).

68. The system of claim 4, wherein said peptide is HKNQT (SEQ ID NO:34).

69. The system of claim 4, wherein said peptide is FKLVG (SEQ ID NO:35).

70. The system of claim 4, wherein said peptide is KKQPK (SEQ ID NO:36).

71. The system of claim 4, wherein said peptide is EKKQT (SEQ ID NO:37).

72. The system of claim 4, wherein said peptide is EKKKK (SEQ ID NO:38).

73. The system of claim 4, wherein said peptide is KKIKQ (SEQ ID NO:39).

74. The system of claim 4, wherein said peptide is KKKKS (SEQ ID NO:40).

75. The system of claim 4, wherein said peptide is KKQKK (SEQ ID NO:41).

76. The system of claim 4, wherein said peptide is KKLNY (SEQ ID NO:42).

77. The system of claim 4, wherein said peptide is DGKKT (SEQ ID NO:43).

78. The system of claim 4, wherein said peptide is KKPTT (SEQ ID NO:44).

79. The system of claim 4, wherein said peptide is KFIFG (SEQ ID NO:45).

80. The system of claim 4, wherein said peptide is FKKMY (SEQ ID NO:46).

81. The system of claim 4, wherein said peptide is FFFKK (SEQ ID NO:47).

82. The system of claim 4, wherein said peptide is KQKKI (SEQ ID NO:48).

83. The system of claim 4, wherein said peptide is HIKKK (SEQ ID NO:49).

84. The system of claim 4, wherein said peptide is DFFHK (SEQ ID NO:50).

85. The system of claim 4, wherein said peptide is AKKKK (SEQ ID NO:51).

86. The system of claim 4, wherein said peptide is AHIKK (SEQ ID NO:52).

87. The system of claim 4, wherein said peptide is AHKKK (SEQ ID NO:53).

88. The system of claim 4, wherein said peptide is LKLVY (SEQ ID NO:54).

89. The system of claim 4, wherein said peptide is PKQKK (SEQ ID NO:55).

90. The system of claim 4, wherein said peptide is AKKKT (SEQ ID NO:56).

* * * * *

UNITED STATES PATENT AND TRADEMARK OFFICE
CERTIFICATE OF CORRECTION

PATENT NO. : 7,041,506 B2
APPLICATION NO. : 09/992124
DATED : May 9, 2006
INVENTOR(S) : Campbell et al.

It is certified that error appears in the above-identified patent and that said Letters Patent is hereby corrected as shown below:

Column 33,

Line 54: "Tyr" should read --Thr--

Column 47,

Line 48: "NO:2 1" should read --NO:21--

Column 49,

Line 34: "polysaceharide" should read --polysaccharide--

Line 53: "IFKFG" should read --FIKFG--

Signed and Sealed this

Tenth Day of April, 2007

JON W. DUDAS
*Director of the United States Patent and Trademark Office*

SEQUENCE LISTING

<160> NUMBER OF SEQ ID NOS: 70

<210> SEQ ID NO 1
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 1

Ile Phe Phe Lys Gly
1               5

<210> SEQ ID NO 2
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 2

```
Phe Ile Lys Phe Gly
1               5

<210> SEQ ID NO 3
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 3

Phe Ile Phe Ala Lys
1               5

<210> SEQ ID NO 4
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 4

Gln Val Val Ala Lys
1               5

<210> SEQ ID NO 5
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 5

Phe Lys Phe Ile Gly
1               5

<210> SEQ ID NO 6
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 6

Ala Phe Phe Lys Ile
1               5

<210> SEQ ID NO 7
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 7

Val Phe Pro Phe Lys
1               5

<210> SEQ ID NO 8
<211> LENGTH: 5
<212> TYPE: PRT
<213> ORGANISM: artificial sequence
<220> FEATURE:
```

<223> OTHER INFORMATION: Synthetic peptide selected for biological
      activity

<400> SEQUENCE: 8

Ala Lys Ile Phe Phe
1               5

<210> SEQ ID NO 9
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 9

Ala Phe Lys Ile Phe
1               5

<210> SEQ ID NO 10
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 10

Lys Phe Ala Phe Ile
1               5

<210> SEQ ID NO 11
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 11

Phe Ala Lys Phe Ile
1               5

<210> SEQ ID NO 12
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 12

Ala Phe Phe Phe Gln
1               5

<210> SEQ ID NO 13
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 13

Glu Glu Glu Met Tyr
1               5

```
<210> SEQ ID NO 14
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 14

Phe Ile Lys Leu Met
1               5

<210> SEQ ID NO 15
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 15

Phe Phe Ile Pro Tyr
1               5

<210> SEQ ID NO 16
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 16

Phe Lys Leu Val Tyr
1               5

<210> SEQ ID NO 17
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 17

Lys Lys Lys Lys Lys
1               5

<210> SEQ ID NO 18
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 18

Lys Lys Lys Lys Leu
1               5

<210> SEQ ID NO 19
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 19
```

```
Phe Lys Lys Lys Gln
1               5

<210> SEQ ID NO 20
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 20

Lys Lys Lys Ser Lys
1               5

<210> SEQ ID NO 21
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 21

Lys Lys Lys Leu Lys
1               5

<210> SEQ ID NO 22
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 22

Phe Lys Lys Lys Lys
1               5

<210> SEQ ID NO 23
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 23

Leu Lys Lys Lys Lys
1               5

<210> SEQ ID NO 24
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 24

Lys Lys Leu Lys Lys
1               5

<210> SEQ ID NO 25
<211> LENGTH: 5
<212> TYPE: PRT
<213> ORGANISM: artificial sequence
```

```
<220> FEATURE:
<223> OTHER INFORMATION: Synthetic peptide selected for biological
      activity

<400> SEQUENCE: 25

Lys Lys Lys Lys Thr
1               5

<210> SEQ ID NO 26
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 26

Lys Lys Pro Lys Lys
1               5

<210> SEQ ID NO 27
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 27

Lys Lys Pro Gln Tyr
1               5

<210> SEQ ID NO 28
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 28

Ser Lys Lys Lys Lys
1               5

<210> SEQ ID NO 29
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 29

Lys Val Lys Lys Lys
1               5

<210> SEQ ID NO 30
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 30

Lys Asn Gln Thr Tyr
1               5
```

```
<210> SEQ ID NO 31
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 31

Phe Lys Lys Lys Val
1               5

<210> SEQ ID NO 32
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 32

Lys Pro Lys Lys Lys
1               5

<210> SEQ ID NO 33
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 33

Phe Phe Lys Lys Lys
1               5

<210> SEQ ID NO 34
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 34

His Lys Asn Gln Tyr
1               5

<210> SEQ ID NO 35
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 35

Phe Lys Leu Val Gly
1               5

<210> SEQ ID NO 36
<211> LENGTH: 5
<212> TYPE: PRT
<213> ORGANISM: artificial sequence
<220> FEATURE:
<223> OTHER INFORMATION: Synthetic peptide selected for biological
      activity
```

```
<400> SEQUENCE: 36

Lys Lys Gln Pro Lys
1               5

<210> SEQ ID NO 37
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 37

Glu Lys Lys Gln Thr
1               5

<210> SEQ ID NO 38
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 38

Glu Lys Lys Lys Lys
1               5

<210> SEQ ID NO 39
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 39

Lys Lys Ile Lys Gln
1               5

<210> SEQ ID NO 40
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 40

Lys Lys Lys Lys Ser
1               5

<210> SEQ ID NO 41
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 41

Lys Lys Gln Lys Lys
1               5

<210> SEQ ID NO 42
<211> LENGTH: 5
<212> TYPE: PRT
```

```
<213> ORGANISM: artificial sequence
<220> FEATURE:
<223> OTHER INFORMATION: Synthetic peptide selected for biological
      activity

<400> SEQUENCE: 42

Lys Lys Leu Asn Tyr
1               5

<210> SEQ ID NO 43
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 43

Asp Gly Lys Lys Thr
1               5

<210> SEQ ID NO 44
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 44

Lys Lys Pro Thr Thr
1               5

<210> SEQ ID NO 45
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 45

Lys Phe Ile Phe Gly
1               5

<210> SEQ ID NO 46
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 46

Phe Lys Lys Met Tyr
1               5

<210> SEQ ID NO 47
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 47

Phe Phe Phe Lys Lys
1               5
```

<210> SEQ ID NO 48
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 48

Lys Gln Lys Lys Ile
1               5

<210> SEQ ID NO 49
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 49

His Ile Lys Lys Lys
1               5

<210> SEQ ID NO 50
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 50

Asp Phe Phe His Lys
1               5

<210> SEQ ID NO 51
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 51

Ala Lys Lys Lys Lys
1               5

<210> SEQ ID NO 52
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 52

Ala His Ile Lys Lys
1               5

<210> SEQ ID NO 53
<211> LENGTH: 5
<212> TYPE: PRT
<213> ORGANISM: artificial sequence
<220> FEATURE:
<223> OTHER INFORMATION: Synthetic peptide selected for biological
      activity

```
<400> SEQUENCE: 53

Ala His Lys Lys Lys
1               5

<210> SEQ ID NO 54
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 54

Leu Lys Leu Val Tyr
1               5

<210> SEQ ID NO 55
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 55

Pro Lys Gln Lys Lys
1               5

<210> SEQ ID NO 56
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 56

Ala Lys Lys Lys Thr
1               5

<210> SEQ ID NO 57
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 57

Asp Glu Glu Thr Tyr
1               5

<210> SEQ ID NO 58
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 58

His Asn Pro Pro Tyr
1               5

<210> SEQ ID NO 59
<211> LENGTH: 5
```

```
<212> TYPE: PRT
<213> ORGANISM: artificial sequence
<220> FEATURE:
<223> OTHER INFORMATION: Synthetic peptide selected for biological
      activity

<400> SEQUENCE: 59

Gly Gly His Met Ser
1               5

<210> SEQ ID NO 60
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 60

Ala Ala Asp Glu Gly
1               5

<210> SEQ ID NO 61
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 61

Gly Gly Gly Gly Ser
1               5

<210> SEQ ID NO 62
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 62

Glu Glu Gly Leu Ser
1               5

<210> SEQ ID NO 63
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 63

His His Pro Ser Thr
1               5

<210> SEQ ID NO 64
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 64

Phe His His Asn Thr
```

```
<210> SEQ ID NO 65
<211> LENGTH: 5
<212> TYPE: PRT
<213> ORGANISM: artificial sequence
<220> FEATURE:
<223> OTHER INFORMATION: Synthetic peptide selected for biological
      activity

<400> SEQUENCE: 65

Ala Asp Glu Leu Asn
1               5

<210> SEQ ID NO 66
<211> LENGTH: 4
<212> TYPE: PRT
<213> ORGANISM: artificial sequence
<220> FEATURE:
<223> OTHER INFORMATION: Synthetic peptide selected for biological
      activity

<400> SEQUENCE: 66

Lys Lys Lys Lys
1

<210> SEQ ID NO 67
<211> LENGTH: 3
<212> TYPE: PRT
<213> ORGANISM: artificial sequence
<220> FEATURE:
<223> OTHER INFORMATION: Synthetic peptide selected for biological
      activity

<400> SEQUENCE: 67

Lys Lys Lys
1

<210> SEQ ID NO 68
<211> LENGTH: 2
<212> TYPE: PRT
<213> ORGANISM: Artificial Sequence
<220> FEATURE:
<223> OTHER INFORMATION: Synthetic peptide selected for biological
      activity

<400> SEQUENCE: 68

Lys Lys
1

<210> SEQ ID NO 69
<211> LENGTH: 3
<212> TYPE: PRT
<213> ORGANISM: Artificial Sequence
<220> FEATURE:
<223> OTHER INFORMATION: Synthetic peptide selected for biological
      activity
<220> FEATURE:
<221> NAME/KEY: MOD_RES
<222> LOCATION: (1)..(3)
<223> OTHER INFORMATION: Orn
<220> FEATURE:
<221> NAME/KEY: MISC_FEATURE
<222> LOCATION: (1)..(3)
<223> OTHER INFORMATION: Orn is in all Xaa locations

<400> SEQUENCE: 69

Xaa Xaa Xaa
1
```

```
<210> SEQ ID NO 70
<211> LENGTH: 3
<212> TYPE: PRT
<213> ORGANISM: Artificial Sequence
<220> FEATURE:
<223> OTHER INFORMATION: Synthetic peptide selected for biological
      activity

<400> SEQUENCE: 70

Arg Arg Arg
1
```